US011060125B2

(12) United States Patent
Shin et al.

(10) Patent No.: US 11,060,125 B2
(45) Date of Patent: Jul. 13, 2021

(54) ELECTROCHEMICAL BIOSENSOR USING DUAL ELECTRODE PAIR

(71) Applicants: SK INNOVATION CO., LTD., Seoul (KR); UNIST (ULSAN NATIONAL INSTITUTE OF SCIENCE AND TECHNOLOGY), Ulsan (KR)

(72) Inventors: Heung Joo Shin, Ulsan (KR); Yeong Jin Lim, Busan (KR); Yun-Jeong Lee, Jeollabuk-do (KR); Sharma Deepti, Ulsan (KR)

(73) Assignees: SK INNOVATION CO., LTD., Seoul (KR); UNIST (ULSAN NATIONAL INSTITUTE OF SCIENCE AND TECHNOLOGY), Ulsan (KR)

(*) Notice: Subject to any disclaimer, the term of this patent is extended or adjusted under 35 U.S.C. 154(b) by 315 days.

(21) Appl. No.: 16/258,326

(22) Filed: Jan. 25, 2019

(65) Prior Publication Data
US 2019/0153499 A1 May 23, 2019

Related U.S. Application Data

(63) Continuation of application No. 15/300,192, filed as application No. PCT/KR2015/003046 on Mar. 27, 2015, now abandoned.

(30) Foreign Application Priority Data

Mar. 28, 2014 (KR) .................. 10-2014-0036876
Mar. 26, 2015 (KR) .................. 10-2015-0042538

(51) Int. Cl.
*C12Q 1/00* (2006.01)
*G01N 27/327* (2006.01)

(52) U.S. Cl.
CPC ............ *C12Q 1/006* (2013.01); *C12Q 1/003* (2013.01); *G01N 27/3271* (2013.01); *G01N 27/3272* (2013.01)

(58) Field of Classification Search
None
See application file for complete search history.

(56) References Cited

U.S. PATENT DOCUMENTS

| 8,880,139 | B1* | 11/2014 | Etzkorn | G01N 27/3271 600/347 |
| 2003/0203498 | A1* | 10/2003 | Neel | C12Q 1/006 436/95 |
| 2004/0060818 | A1* | 4/2004 | Feldman | C12Q 1/001 204/403.01 |
| 2005/0051427 | A1* | 3/2005 | Brauker | A61B 5/076 204/412 |
| 2013/0284610 | A1* | 10/2013 | Wilsey | G01N 27/3275 205/777.5 |

(Continued)

OTHER PUBLICATIONS

Shabani et al., Talanta, 70 (2006) 615-623. (Year: 2006).*

*Primary Examiner* — Eli S Mekhlin
(74) *Attorney, Agent, or Firm* — IP & T Group LLP

(57) ABSTRACT

An electrochemical biosensor using a sensing system includes a working electrode including an active surface modified through a linker; and an auxiliary electrode. The sensor has a high current value compared with an existing sensor and retains excellent stability and sensitivity, and thus can be expected to be easily used for sensing various kinds of biomaterials.

7 Claims, 12 Drawing Sheets

(a)

(b)

(56) References Cited

U.S. PATENT DOCUMENTS

2014/0174950 A1* 6/2014 Gooding ............ G01N 27/3271
 205/777.5
2014/0197041 A1* 7/2014 Ching ................ G01N 27/3271
 205/777.5

* cited by examiner

[FIG. 1]
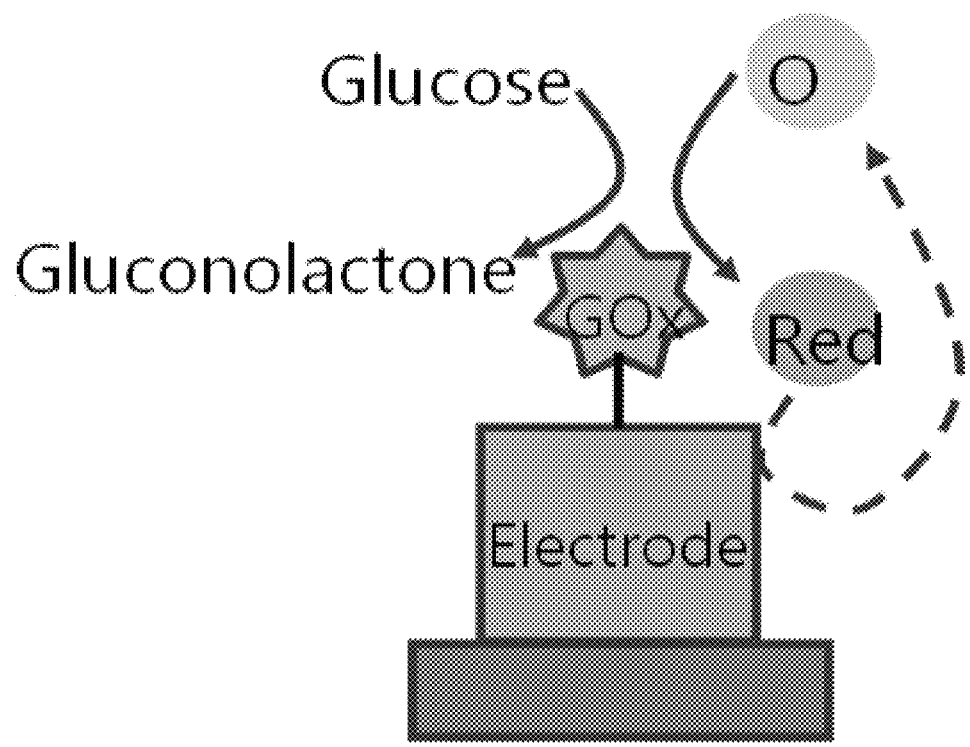

[FIG. 2]
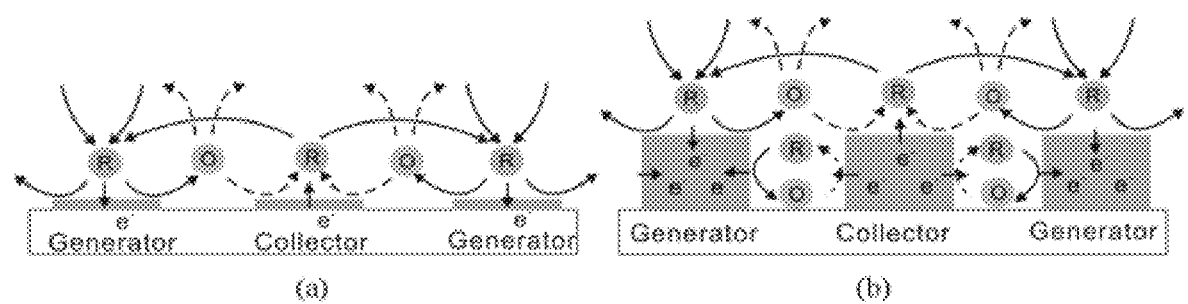

[FIG. 3]
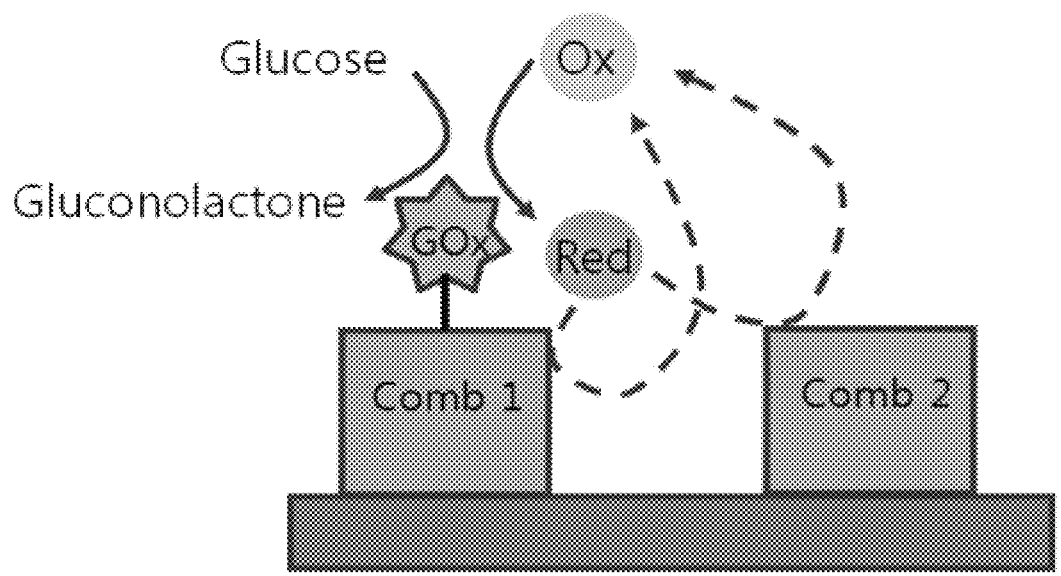

[FIG. 4]
(A)
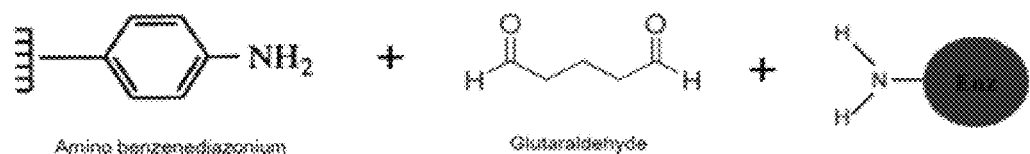
(B)
EDC (1-ethyl-3-(-3-dimethylaminopropyl) carbodiimide hydrochloride
NHS N-hydroxysuccinimide

[FIG. 5]
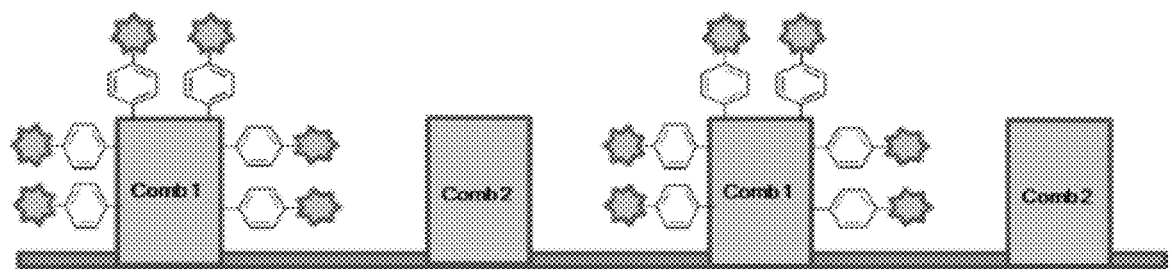

[FIG. 6]
Step 1: Reduction of diazonium salt on electrode surface.
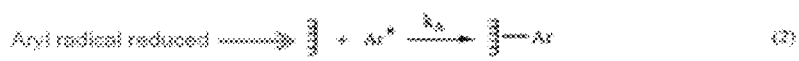
Step 2: Reduction of nitro to amino terminal.
Step 3: Immobilization of enzyme
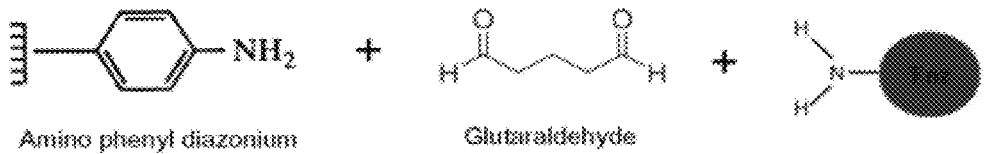
Amino phenyl diazonium      Glutaraldehyde

[FIG. 7]
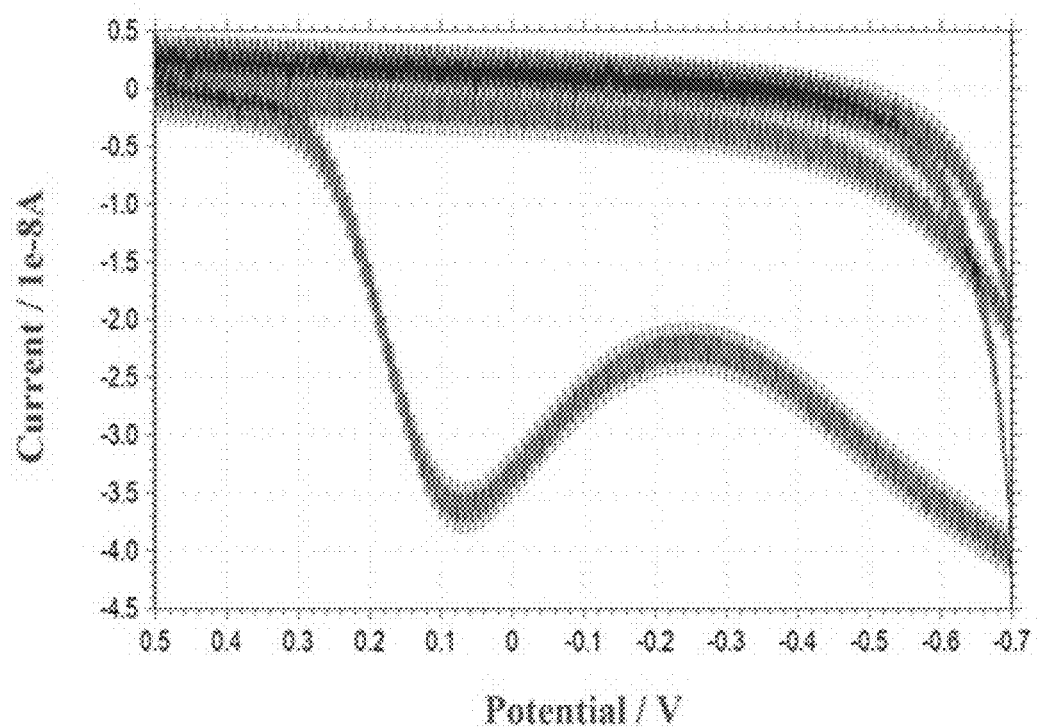

[FIG. 8]
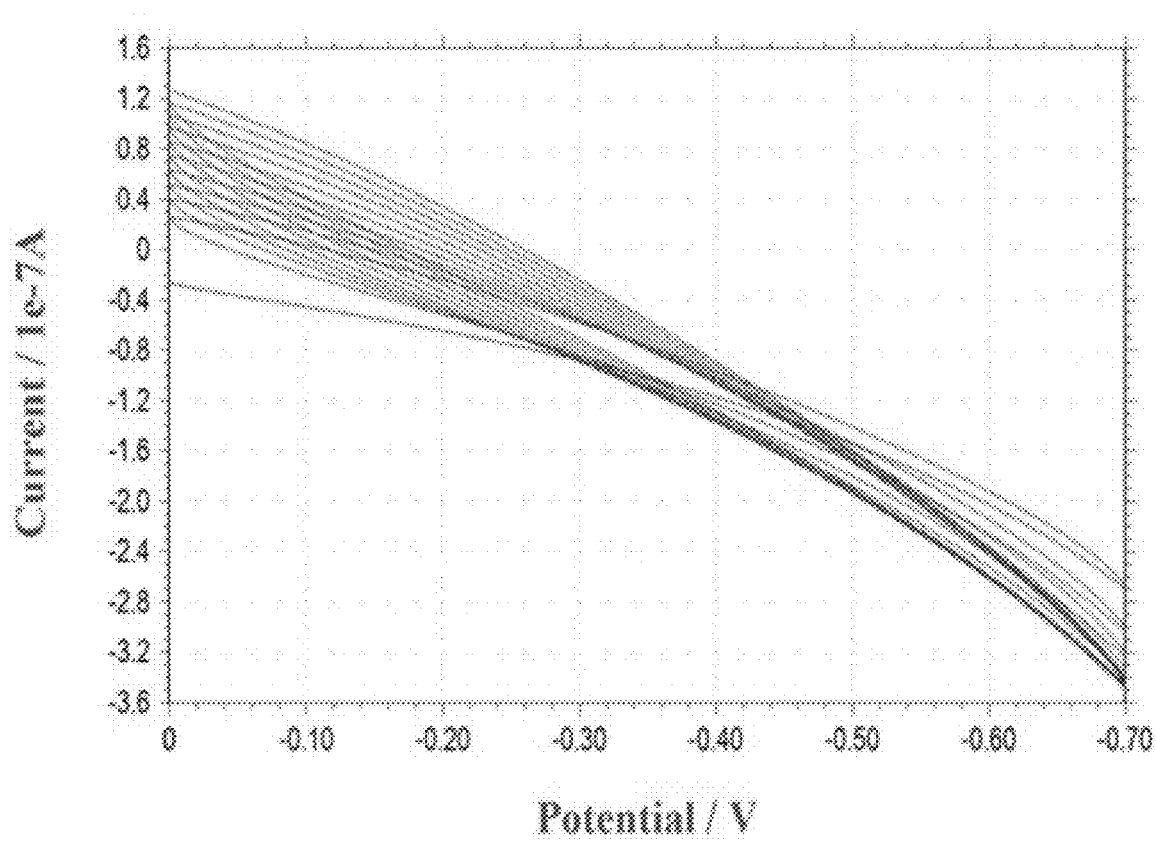

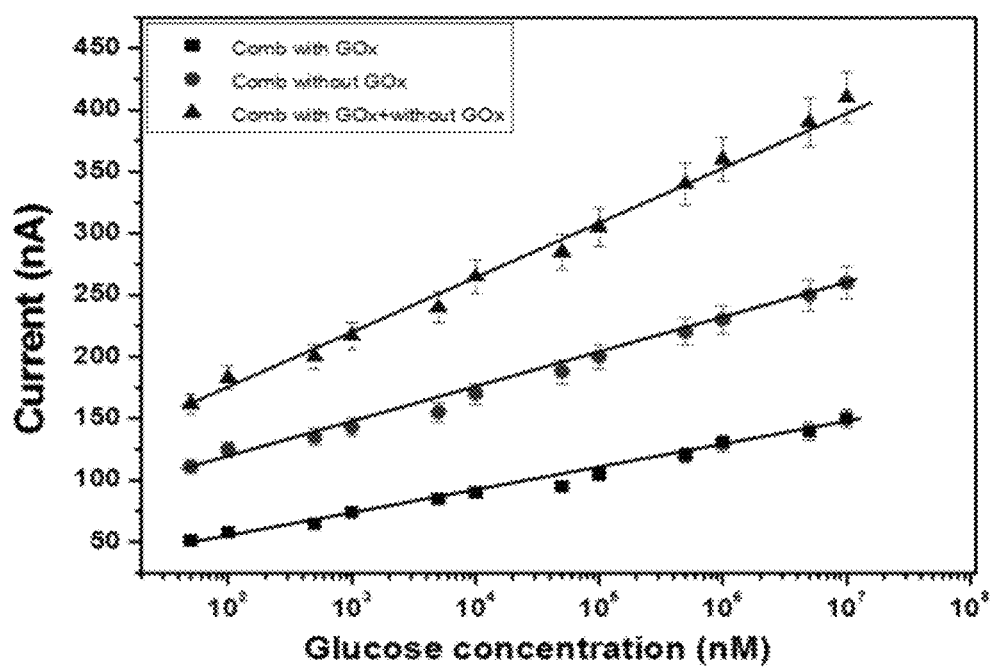
[FIG. 9]

[FIG. 10]
(A)
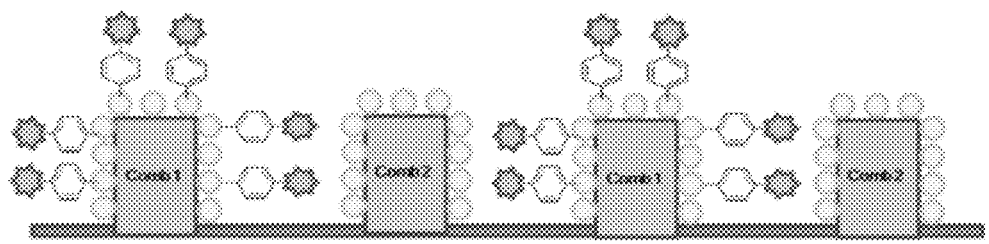
(B)
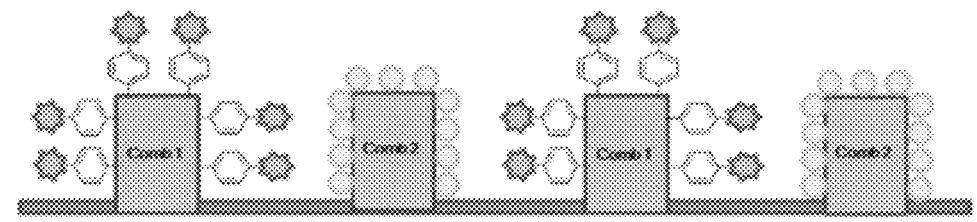
- Nanoparticles (eg. Gold)
- Biomolecule
- Diazonium salt

[FIG. 11]
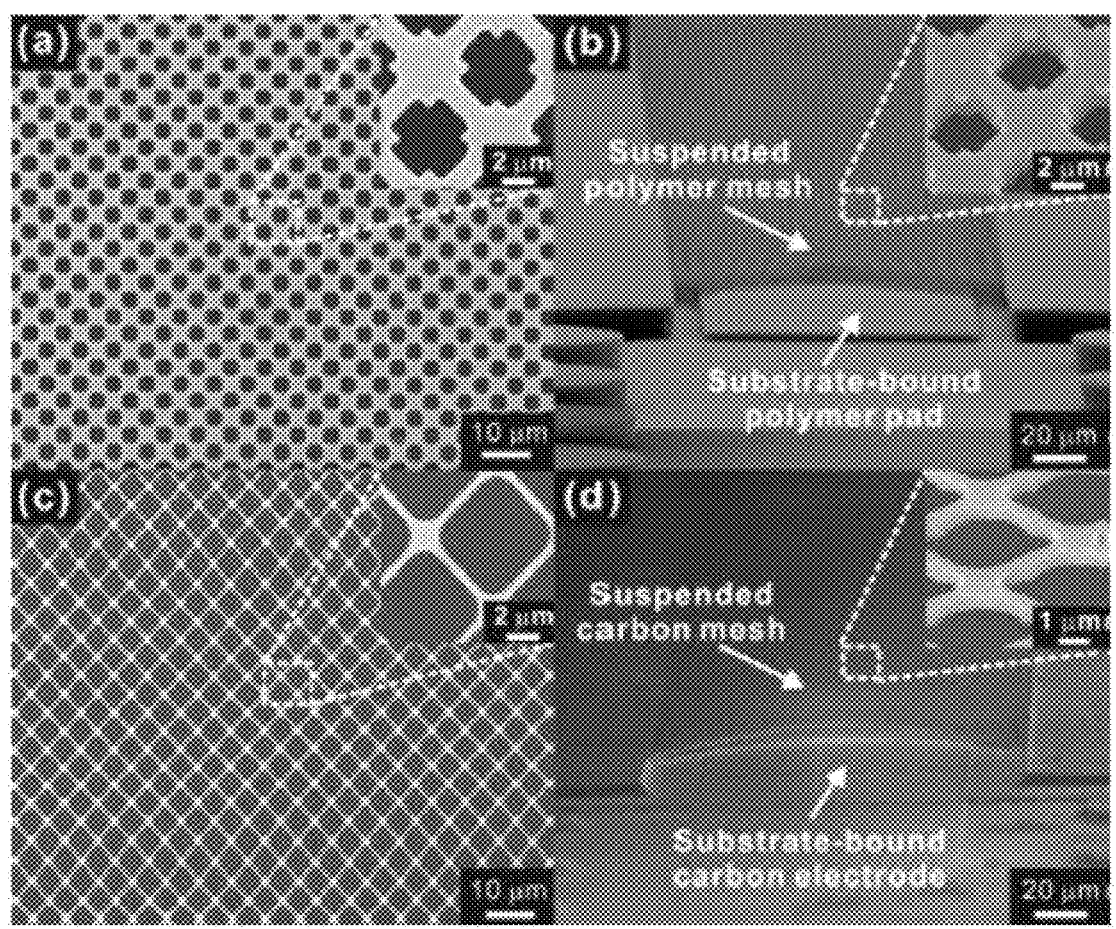

[FIG. 12]
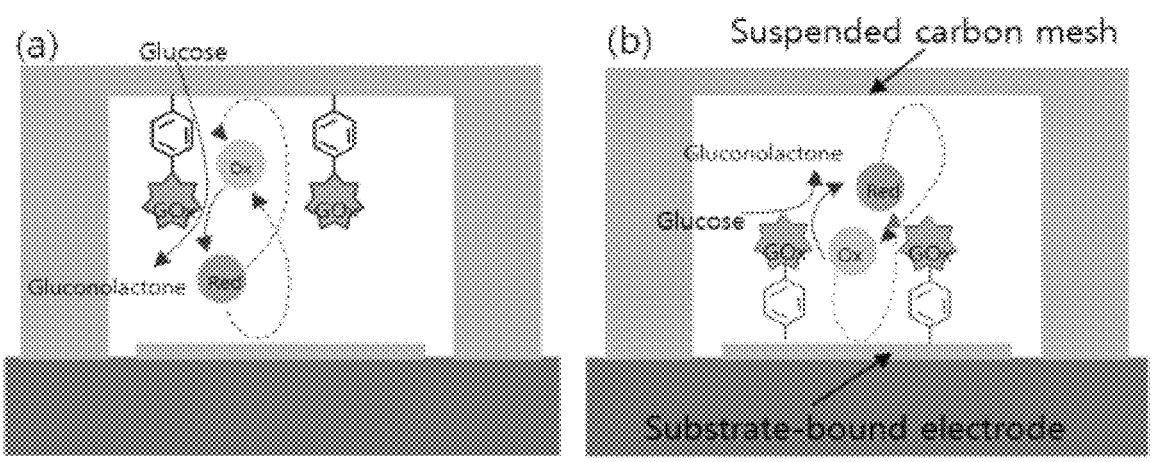

ELECTROCHEMICAL BIOSENSOR USING DUAL ELECTRODE PAIR

CROSS-REFERENCE TO RELATED APPLICATION

This application is a continuation of U.S. patent application Ser. No. 15/300,192 filed on Sep. 28, 2016, now abandoned, which is a national stage application of PCT/KR2015/003046 filed on Mar. 27, 2015, which claims priority of Korean patent application number 10-2014-0036876 filed on Mar. 28, 2014 and Korean patent application number 10-2015-0042538 filed on Mar. 26, 2015. The disclosure of each of the foregoing applications is incorporated herein by reference in its entirety.

TECHNICAL FIELD

The embodiment of the embodiment of the present invention relates to an electrochemical sensor, and more particularly, to an electrochemical biosensor using a sensing system including a working electrode containing an active surface modified by a linker, and an auxiliary electrode.

BACKGROUND ART

One of the goals of nanomedicine in life science is to study various biological processes in a laboratory, in which nanomaterials are compatible. Since most of the biochemical processes involve in vivo electron transfer, it has received attention in an electrochemical field. In that field, the development of a new form of the electrochemical biosensor to which an enzyme or other biomaterials are linked together with the nanomaterials has become important. Glucose is a very common fuel in biology, and used as an energy source in most organisms ranging from microorganisms to humans. The concentration of glucose in human blood is 4.4 to 6.6 mM. Therefore, it is necessary to develop a continuous quantitative detection method of glucose in blood, urine, and other body fluid. Since an abnormal increase in a glucose level causes diabetes, it is an important factor to detect glucose. Up to date, various conductive polymers such as polyaniline, polypyrrole or polyindole have been used for glucose sensing. However, this method needs long process time, and involves complicated chemical synthesis which increases production cost. In addition, self-assembled monolayer (SAM) is widely used for covalent bonding of glucose oxidase. However, the sensitivity of a glucose sensor is generally resulted from the compromise between low stability of SAMs and limited potential window. Therefore, in order to overcome the limitations of SAMs, the study of reductive adsorption of an aryl diazonium salt in a carbon electrode has been conducted. The study may be applied for sensing on not only all kinds of carbon surfaces (glass carbon, graphite, surface printed electrode carbon nanotube diamond) but also metal, silicone and indium tin oxide. The electrochemical reduction of a diazonium salt has been successfully used in order to form various functional groups in a carbon electrode for immobilizing biomolecules. However, adsorbing a diazonium salt on a nano-sized electrode still remains as a challenge.

Most of the recent studies of a glucose sensor are based on immobilization of enzymes, such as glucose oxidase promoting oxidation of glucose to gluconolactone such as in Korean Patent Laid-Open Publication No. 10-2000-0008880, or glucose dehydrogenase such as in Korean Patent Laid-Open Publication Nos. 10-2010-0131495 and 10-2005-0019139. In most cases, a sensor based on an enzyme needs a charge carrier for improving the sensitivity and selectivity of the sensor. However, a current measuring enzyme electrode has relatively low output current and sensitivity, and has a problem in that the reaction time is delayed.

In particular, when measuring a glucose level in blood of a diabetic patient, ion attraction of various interfering substances in blood should be alleviated by applying an extremely low voltage (0.055 V or less), and a rapid enzyme oxidation reaction needs to be induced, and thus, there needs to develop a glucose sensor facilitating a high current density and excellent sensitivity with a low voltage input.

DISCLOSURE

Technical Problem

An object of the embodiment of the present invention is to provide a glucose sensor provided with nanoelectrodes facilitating high output current density, efficient charge transfer, high surface to volume ratio, and excellent sensitivity.

Technical Solution

In one general aspect,
an electrochemical sensor for determining presence or concentration of an analyte in a fluid includes:
a substrate; and
working electrodes formed on the substrate, and having an enzyme attached thereon by a linker.

The electrochemical sensor may form a matrix in which P working electrodes (P is a natural number of 1 or more) are arranged longitudinally and/or transversely.

The immobilization of biomolecules on a single electrode surface allows direct electron transfer between the electrode and an enzyme. FIG. 1 is a schematic view illustrating glucose sensing using a single electrode coated with glucose oxidase. In FIG. 1, glucose in a specimen solution and oxygen indicated as 'O' are reacted in the presence of glucose oxidase to produce gluconolactone and hydrogen peroxide indicated as 'Red'. By collecting the oxidation current of the hydrogen peroxide, glucose concentration in the electrode may be measured. After hydrogen oxidation in the electrode, oxygen as the product is transferred to an enzyme site to undergo a reduction reaction. Through repetition of the redox reactions as such, a current level may be raised. However, generally the current level obtained by using the strategy becomes very low due to the reduction in surface reactivity caused by enzyme coating and limited electrode surface area. Therefore, in order to obtain a high current level, the study of electrode geometry is needed.

In order to improve a redox current level, the study of an IDA (interdigitated array) nanoelectrode is actively conducted. The electrode may be manufactured using various kinds of conductive materials such as carbon, gold, platinum, palladium, and conductive polymers. The IDA nanoelectrode may include two comb-shaped electrodes. As in FIG. 2, the redox reactions of electrochemical reversible redox species are recycled between electrodes; this amplifies a current signal with the number of recycles. The current signal amplification by redox cycling depends on mass transfer of the redox species between electrodes. Particularly, the mass transfer through diffusion at micro/nanoelectrodes may be improved by reducing the gap between the electrodes, and increasing the aspect ratio of the electrodes.

Redox mediators play an important role in the detection of various molecules using the electrochemical sensor. The mediators transfer electrons between enzymes and electrodes through electrochemical-enzyme redox cycling. In the reaction mechanism of glucose oxidase (GOx), oxygen rapidly reacts with GOx in a reduced form to produce hydrogen peroxide as a byproduct of the reaction. Here, oxygen may be replaced with various forms of redox mediators such as ruthenium, a hexamine complex, ferricyanide, ferrocenemethanol and ferrocenemonocarboxylic acid. The electron mediators undergo rapid electron transfer reactions on electrode surface and a rapid electron transfer reaction with a redox enzyme. For example, redox reactions using ferricyanide may occur as follows:

Glucose+GOx(FAD)→Gluconic acid+GOx(FADH$_2$)+ 2H$^+$ [Reaction Formula 1]

GOx(FADH$_2$)+[Fe(CN)$_6$]$^{3-}$→GOx(FADH)+[Fe(CN)$_6$]$^{4-}$+H$^+$ [Reaction Formula 2]

GOx(FADH$_2$)+[Fe(CN)$_6$]$^{3-}$→GOx(FADH)+[Fe(CN)$_6$]$^{4-}$ [Reaction Formula 3]

In the embodiment of the embodiment of the present invention, the linker is not limited, but may be attached on nanoparticles directly formed on the electrode.

In the embodiment of the embodiment of the present invention, the nanoparticles are not limited, but may be selected from the group consisting of gold, platinum and palladium.

In another exemplary embodiment of the embodiment of the embodiment of the present invention, the electrochemical sensor may further include an auxiliary electrode formed to be spaced apart from the working electrode in a horizontal direction of the substrate.

In the embodiment of the embodiment of the present invention, the electrochemical sensor of the embodiment of the embodiment of the present invention may include M×N units (M and N are a natural number more than 1, respectively) wherein the unit is a pair of the one working electrode and one auxiliary electrode, and M units are arranged to be spaced apart in a longitudinal direction, and N units are arranged to be spaced apart in a transverse direction, thereby forming a M×N matrix.

As illustrated in FIG. 3, the glucose oxidase may be selectively immobilized only on any one of the IDA electrodes (comb 1), through which a reduced species may be oxidized more efficiently on the other electrode (comb 2) which is not coated with any material resulting in higher electrochemical reactivity at surface. Thus, high signal amplification as compared with the sensing based on a single electrode is possible. As the two electrodes are more closely spaced, the current level may be improved. The enzyme may be selectively immobilized on a certain electrode by reducing the aryl diazonium salt.

As mentioned above, in the present glucose sensor, oxygen may be replaced with various forms of redox mediators such as ruthenium, a hexamine complex, ferricyanide, ferrocenemethanol and ferrocenemonocarboxylic acid, which may be recycled between the enzyme and the electrode. The redox species may be electrochemically reacted on an electrode surface without hydrolysis which limits stable glucose sensing when using oxygen as the redox species.

In the embodiment of the embodiment of the present invention, the analyte-enzyme is not limited, however, may be selected from the group consisting of glucose-glucose oxidase; glucose-glucose dehydrogenase; adenosine triphosphate-glucose oxidase and hexokinase; cholesterol-cholesterol oxidase (ChOx) and cholesterol esterase; and lactate-lactate dehydrogenase.

As in FIG. 4, diazonium salt binding may provide various functional groups such as —NH$_2$ and —COOH which allow various biomolecules to be linked on the electrode surface. Further, as in FIG. 5, selective linkage of biomolecules on an IDA nanoelectrode based on diazonium may contribute to the detection of various types of molecules as follows:

(a) glucose using glucose oxidase (GOx),

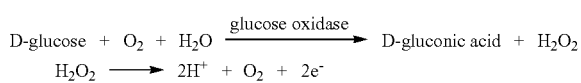

(b) adenosine triphosphate (ATP) using glucose oxidase and hexokinase,

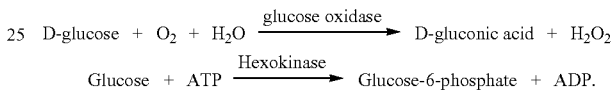

(c) cholesterol using cholesterol oxidase (ChOx) and cholesterol esterase,

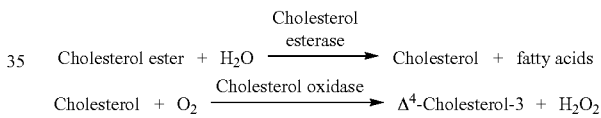

(d) lactate using lactate dehydrogenase.

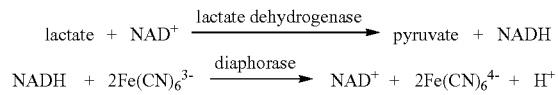

Another exemplary embodiment of the embodiment of the embodiment of the present invention relates to an electrochemical sensor including electrodes having a mesh shape that are separated apart from the substrate in a vertical direction.

In the embodiment of the embodiment of the present invention, the sensor may further include an auxiliary electrode formed under the working electrode while having a space therebetween, but not limited thereto.

The electrochemical sensor manufactured in the form of a mash-shaped electrode may represent better efficiency in redox cycling, as compared with that using the IDA nanoelectrode.

In the embodiment of the embodiment of the present invention, the linker may be formed by converting a functional group of a surface-modified base material including diazonium, a diazonium salt or a derivative thereof into an amine group, and then mixing the surface-modified base material with a dialdehyde crosslinking agent, and attach the biomaterial on an electrode surface.

In another general aspect, a method of manufacturing an electrochemical sensor includes:

forming an electrode on a substrate;

forming a surface-modified base material on the electrode;

reacting the surface-modified base material and a crosslinking agent; and reacting the reacted crosslinking agent and an enzyme, thereby attaching the enzyme on the electrode.

In the embodiment of the embodiment of the present invention, the surface-modified base material is not limited, but may use diazonium, a diazonium salt or a derivative thereof, and more preferably, as the surface-modified base material, 4-nitrophenyl diazonium tetrafluoroborate (4-NP) may be used.

In the embodiment of the embodiment of the present invention, the crosslinking agent is not limited as long as it is a dialdehyde-based compound, but for example, it may be selected from the group consisting of glyoxal, malondialdehyde, succindialdehyde, glutaraldehyde and phthalaldehyde, and preferably, may be glutaraldehyde.

In another exemplary embodiment of the embodiment of the embodiment of the present invention, the method of manufacturing an electrochemical sensor may further include forming nanoparticles on the electrode, wherein the surface-modified base material is directly formed on the nanoparticle.

In the embodiment of the embodiment of the present invention, the nanoparticle is not limited, but preferably gold, platinum or palladium may be used.

In carrying out biosensing using the IDA nanoelectrode through coating of the nanoparticles, various nanoparticles are coated on an electrode surface, thereby obtaining electrochemically improved properties. This may improve the surface area and reactivity of the electrode, thereby improving an electrochemical signal.

In the embodiment of the present invention, the electrode may be an IDA (interdigitated array) nanoelectrode, but not limited thereto.

In the embodiment of the present invention, the gap between the working electrode and the auxiliary electrode may be 10 nm to 10 μm, but not limited thereto.

As recognized in an exemplary embodiment of the embodiment of the present invention, by determining the distance between the working electrode and the auxiliary electrode within the range of the gap listed above, the redox reaction occurs more actively, thereby obtaining a higher level of current.

Advantageous Effects

The sensor of the embodiment of the present invention has a higher current value as compared with a conventional sensor, and excellent stability and sensitivity, and thus, it is expected that the sensor may be easily used for sensing various kinds of biomaterials.

DESCRIPTION OF DRAWINGS

FIG. 1 is a schematic view of glucose sensing using a single electrode functionalized by glucose oxidase.

FIG. 2 is a schematic view of redox cycling in (a) IDA electrodes having a thin band shape, and (b) IDA electrodes having a high aspect ratio.

FIG. 3 is a schematic view of glucose sensing using IDA electrodes selectively functionalized by glucose oxidase.

FIG. 4 is enzyme immobilization using a diazonium-modified electrode.

FIG. 5 is a schematic view for selective immobilization of biomolecules using a diazonium salt.

FIG. 6 is a schematic process chart of selective electrode functionalization.

FIG. 7 is a graph of cyclic voltammogram curves of carbon IDA nanoelectrodes (comb 1) in a solution of 1 mM 4-nitrophenyl diazonium tetrafluoroborate (4-NP) and 0.1 M tetrabutylammonium tetrafluoroborate/acetonitrile at a scan speed of 200 mV/sec.

FIG. 8 is a graph of cyclic voltammogram curves for reducing a nitro group of 4-NP to an amino group in 0.1 M KCl+deionized water/ethanol (9:1) at a scanning speed of 100 mV/sec.

FIG. 9 is a drawing representing oxidation current values collected at IDA electrodes depending on glucose concentrations using carbon IDA nanoelectrodes.

FIG. 10 is a schematic view representing immobilization of biomolecules on IDA nanoelectrodes modified with metal nanoparticles, wherein (A) both electrodes are coated with nanoparticles, and (B) only one electrode (comb) is coated with nanoparticles.

FIG. 11 is SEM images of a stacked polymer setbefore pyrolysis (a, b), and the stacked carbon electrode set after pyrolysis (c, d).

FIG. 12 is a schematic view of glucose sensing using a stacked electrode set selectively modified with enzymes.

BEST MODE

Hereinafter, the embodiment of the present invention will be described in detail with reference to the following examples and accompanying drawings. However, they are for describing the embodiment of the present invention in more detail, and the scope of the embodiment of the present invention is not limited thereto.

(Chemical Materials)

Acetonitrile (Fisher Scientific), tetrabutylammonium tetrafluoroborate ($NBu_4BF_4$, Fluka), 4-nitrophenyl diazonium tetrafluoroborate (4-NP), potassium ferricyanide, potassium ferrocyanide, glutaraldehyde, potassium chloride, sodium cyanoborohydride, *Aspergillus niger*-derived glucose oxidase (Type X-S, 100,000-250,000 units/g solid, Sigma Aldrich), and phosphate buffer (PBS, pH 7.4; Life Technologies).

(Preparation Example 1) Electrode Manufacturing

A carbon IDA nanoelectrode was manufactured on a 6 inch (100) silicon wafer (Si wafer).

First, a 700-nm-thick silicon dioxide ($SiO_2$) layer was deposited on the silicon wafer by thermal oxidation. An SU-8 negative photoresist IDA structures were patterned using photolithography. In order to convert the photoresist structures into carbon electrodes, the predefined photoresist IDA patterns were pyrolyzed at 900° C. in a vacuum condition. During the pyrolysis, the size of the IDA structure was reduced by 60% in width, and by 90% in height. Finally, the carbon electrodes were passivated except for the interdigitated electrode area.

(Preparation Example 2) Selective Surface Functionalization

As in Example 6, the immobilization of an enzyme may include three steps. 4-nitrophenyl diazonium tetrafluoroborate (4-NP) was used as a base. In order to link the enzyme to diazonium, the functional group of diazonium was converted into an amine group, and glutaraldehyde was used between the amine group of diazonium and the enzyme.

Electrochemical Adsorption of 4-NP

The electrochemical modification of the carbon electrode was measured by scanning electric potential of the electrode from 0.5 to −0.7 V at a scan rate of 200 mV/s vs a Ag/AgCl reference electrode, in acetonitrile containing 1 mM 4-NP in 0.1 M NBu$_4$BF$_4$. Before modification, impurities were removed from the solvent using argon gas for 30 minutes. After modification, the electrodes were washed with deionized water (DI water) for 30 minutes.

Reduction of Nitro Group to Amine Group

For production of an amine group by reducing a nitro group, a protic solvent containing 0.1 M potassium chloride and water/ethanol (90:10, v/v) was used. The potential of the electrode was measured by scanning the electric potential of the electrode from 0 to 0.8 V at a scan rate of 100 mV/s vs a Ag/AgCl reference electrode.

Enzyme Immobilization

For enzyme immobilization via a linker, glutaraldehyde was used as a bifunctional crosslinking agent. After converting the amine group, the carbon IDA electrodes were soaked in 200 μL of 0.1% sodium cyanoborohydride and 2.5 wt % glutaraldehyde solution for 2 hours, and then taken out. Thereafter, the electrodes were cleaned with deionized water, and dried using nitrogen gas. In order to couple a glucose oxidase enzyme to an aldehyde group produced on a carbon electrode, the electrodes were incubated in a buffer solution containing 0.1% sodium cyanoborohydride and 10 mg/mL glucose oxidase in a 50 mM PBS buffer (pH 7.4) at 4° C. overnight.

(Preparation Example 3) Electrochemical Characterization of Electrodes

All electrodes were characterized using cyclic voltammetry by scanning electric potential of the electrodes from 0 to 0.6 V at a scan rate of 50 mV/s to a Ag/AgCl reference electrode in 0.5 M potassium chloride and 10 mM [Fe(CN)$_6$]$^{4-}$ in deionized water. Glucose sensing was carried out using 10 mM [Fe(CN)$_6$]$^{3-}$ as a redox mediator in 0.5 mM PBS (pH 7.4).

A glucose solution was prepared at a concentration of 0.1 M in 100 mM PBS, and subjected to mutarotation at room temperature for 24 hours so as to reach anomeric equilibrium. All solutions for glucose sensing were cleaned by emitting argon gas to the solutions for at least 30 minutes before carrying out an electrochemical test. As a counter electrode, platinum wire was used. Electrochemical detection was carried out using a multi-potentiostat(CHI 1020; CH Instrument Inc., USA).

(Example 1) Surface-Modification of Carbon IDA Nanoelectrode

Carbon IDA nanoelectrodes were manufactured by the procedure of above Preparation Example 1. As illustrated in FIG. 3, the surface of the carbon IDA nanoelectrode was functionalized using a linker and an enzyme. One comb of the carbon IDA nanoelectrodes was functionalized with glucose oxidase (GOx), while the other adjacent comb was used for collecting oxidation current of a ferrocyanide redox species.

FIG. 7 illustrates a cyclic voltammogram in 1 mM 4-NP and 0.1 M NBu$_4$BF$_4$/acetonitrile solution in one comb. The irreversible reduction curve at −0.05 V in the first cycle contributed to the formation of 4-nitrophenyl radical from a diazonium salt derivative. The fact that the first irreversible curve disappears in the second scan means that the nitrophenyl group binded to the carbon surface blocks electron transfer. From the last reversible curve, it is shown that a radical anion formed by dissociation is reduced to an aryl anion on the carbon electrode surface.

The result of reducing a nitro group to an amine group in Preparation Example 2 is illustrated in FIG. 8. The increase in reduction current allows the nitro group to be converted to the amine group.

The amine group activating the carbon electrode was incubated with glucose oxidase using 2.5% glutaraldehyde. Finally, one of the carbon IDA nanoelectrodes was functionalized with glucose oxidase using the method of Preparation Example 2, and the adjacent electrode was used for collecting oxidation current of ferrocyanide.

(Example 2) Glucose Sensing

Glucose sensing was carried out in the presence of a ferricyanide redox mediator having rapid electron transfer kinetics and a stable oxidation/reduction form.

During enzyme reaction, glucose molecules were oxidized by the flavin-adenine dinucleotide (FAD) redox key element of the glucose oxidase enzyme. In the oxidation process, FAD was reduced to FADH$_2$(GOx$_{red}$) as described in the following Reaction Formula 4. In this system, oxygen in the reaction of the Reaction Formula 5 may be replaced with ferricyanide as an alternative electron receptor. Thereafter, FADH$_2$ was oxidized back to FAD, as [Fe(CN)$_6$]$^{3-}$ was reduced to [Fe(CN)$_6$]$^{4-}$ as in Reaction Formulae 6 and 7. The reaction occurred at the carbon electrode (comb 1) functionalized with glucose oxidase, whereas [Fe(CN)$_6$]$^{4-}$ was oxidized back to [Fe(CN)$_6$]$^{3-}$ in the electrode (comb 1) and an adjacent carbon electrode (comb 2), as illustrated in FIG. 3. The reaction in the final step produced measurable current in direct proportion to glucose concentration as the oxidation form of the mediator was regenerated.

Glucose+FAD→Gluconic acid+FADH$_2$+2H$^+$     [Reaction Formula 4]

FADH$_2$+O$_2$→FAD+H$_2$O$_2$     [Reaction Formula 5]

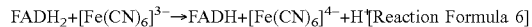
FADH$_2$+[Fe(CN)$_6$]$^{3-}$→FADH+[Fe(CN)$_6$]$^{4-}$+H$^+$ [Reaction Formula 6]

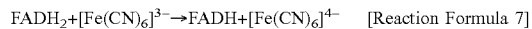
FADH$_2$+[Fe(CN)$_6$]$^{3-}$→FADH+[Fe(CN)$_6$]$^{4-}$     [Reaction Formula 7]

From the above results, redox cycling occurred between the enzyme and the two carbon IDA nanoelectrode combs. In the carbon electrode (comb 1) modified with glucose oxidase, an enzyme reaction including glucose oxidation and [Fe(CN)$_6$]$^{3-}$ reduction occurred. However, in the modified carbon electrode (comb 1) and the non-modified adjacent carbon electrode (comb 2), [Fe(CN)$_6$]$^{4-}$ oxidation reaction occurred. Therefore, it is recognized that both electrodes in the IDA nanoelectrodes participate in the redox cycling of ferricyanide, which contributes to impart high sensitivity in glucose detection.

In FIG. 9, it is shown that as the glucose concentration increases at the two electrodes of the IDA nanoelectrodes, current increases linearly. The current in comb 2 is higher than that in comb 1, since though the distance between enzyme sites and the electrode surface area in comb 2 are longer and larger than those in comb 1, the non-modified surface in comb 2 has higher surface reactivity than that in comb 1 which is modified with multiple molecules. Therefore, it was possible to collect more current using the IDA nanoelectrodes using the carbon electrode not further modified.

(Preparation Example 4) Biosensor Using IDA (Interdigitated Array) Nanoelectrodes Modified with Metal Nanoparticles Similar to the manufacturing method of the electrodes of Preparation Examples 1 and 2, nanoparticles such as gold, platinum or palladium were coated on a carbon electrode before attaching a linker using a diazonium salt thereto as in FIG. 10, thereby manufacturing a biosensor in which biomolecules containing glucose oxidase linked to the electrode through the nanoparticles.

(Preparation Example 5) Glucose Sensing Using Stacked Carbon Electrode Set

As in FIG. 11, a stacked electron set including a suspended carbon mesh and a substrate-bound plane electrode was manufactured as a replacement for the IDA electrodes for using as a biosensor platform similar to the method described in Preparation Examples 1 and 2. For the redox mechanism and manufacturing process for the biosensing, the methods described in Preparation Examples 1 to 3 were used.

It was confirmed that the stacked electrode set manufactured as above showed good efficiency in the redox cycling, as compared with that using the IDA nanoelectrode.

For glucose sensing, the selective diazonium modification of the suspended nanomesh was carried out by the electrochemical reductive adsorption of 4-NP as described in Preparation Example 2. Thereafter, glucose oxidase was immobilized using glutaraldehyde. As in (a) of FIG. 12, the plane electrode was left without any modification for redox cycling of the ferricyanide/ferrocyanide redox couple.

As a different method from that of the electrode manufactured above, as illustrated in (b) of FIG. 12, a method of attaching and modifying the substrate-bound plane electrode as in the method of Preparation Example 2 was used for enzyme immobilization, thereby manufacturing the electrode.

For each of (a) and (b) in FIG. 12, the redox couple was recycled between the enzyme and the electrode surface, and oxidation current on the electrode surface was measured, thereby measuring glucose concentration.

The invention claimed is:

1. A method for determining a-concentration of glucose in a fluid using an electrochemical sensor including a substrate; a working electrode formed on the substrate and having glucose oxidase attached thereon by a linker; and an auxiliary electrode formed to be separated apart from the working electrode in a horizontal direction of the substrate; wherein the working electrode and the auxiliary electrode are interdigitated array electrodes, the method comprising:

contacting the glucose in the fluid to the working electrode and the auxiliary electrode of the electrochemical sensor in a presence of redox species which is recycled, between the working electrode and the auxiliary electrode, measuring a current of the working electrode and the auxiliary electrode, and determining the concentration of the glucose in the fluid using the measured current, wherein the measured current is a sum of a current collected by the working electrode resulted from direct electron transfer between the working electrode and the enzyme and collected by the working electrode, a reduction current of the redox species collected by the working electrode, and an oxidation current of the redox species collected b the auxiliary electrode.

2. The method of claim 1, wherein the linker is attached on nanoparticles directly formed on the electrode.

3. The method of claim 2, wherein the nanoparticles are selected from the group consisting of gold, platinum and palladium.

4. The method of claim 1, wherein the redox species are selected from ruthenium, hexamine complex, ferricyanide, ferrocenemethanol and ferrocenemonocarboxylic acid.

5. The method of claim 1, wherein a gap between the working electrode and the auxiliary electrode is 10 nm to 10 µm.

6. The method of claim 1, wherein the auxiliary electrode is a non-coated electrode.

7. A method for determining a concentration of glucose in a fluid using an electrochemical sensor including a substrate, a working electrode having glucose oxidase attached thereon by a linker is formed to be separated apart from the substrate in a vertical direction, and has a mesh shape, and an auxiliary electrode formed under the working electrode while having a space therebetween, wherein the working electrode and the auxiliary electrode are interdigitated array electrodes, the method comprising:

contacting the glucose in the fluid to the working, electrode and the auxiliary electrode of the electrochemical sensor in a presence of redox species which is recycled between the working electrode and the auxiliary electrode, measuring an oxidation current of the working electrode and the auxiliary electrode, and determining the concentration of the glucose in the fluid using the oxidation current, wherein the oxidation current is a sum of a current collected by the working electrode resulted from direct electron transfer between the working electrode and the enzyme and collected the working electrode, a reduction current of the redox species collected by the working electrode, and an oxidation current of the redox species collected by the auxiliary electrode.

\* \* \* \* \*